(12) United States Patent
Teller

(10) Patent No.: US 6,454,162 B1
(45) Date of Patent: Sep. 24, 2002

(54) PROCESS FOR CONTROLLING THE MISUSE OF DISPOSABLE MEDICAL PRODUCTS

(76) Inventor: David Teller, 530 Alameda del Prado, Novato, CA (US) 94949

( * ) Notice: Subject to any disclaimer, the term of this patent is extended or adjusted under 35 U.S.C. 154(b) by 15 days.

(21) Appl. No.: 09/768,599

(22) Filed: Jan. 25, 2001

(51) Int. Cl.$^7$ ............................................. G06F 17/00
(52) U.S. Cl. ..................................... 235/375; 235/385
(58) Field of Search ................................ 235/375, 385

(56) References Cited

U.S. PATENT DOCUMENTS 6,156,575 A * 12/2000 Fossbind et al. ............. 235/375

FOREIGN PATENT DOCUMENTS

EP 0 738 986 * 10/1996

* cited by examiner

Primary Examiner—Harold I. Pitts
(74) Attorney, Agent, or Firm—Jagtiani + Guttag

(57) ABSTRACT

A process for controlling the miss use of disposable medical products with the steps of: a unique ID code secured to a disposable medical accessory product, a control circuit built into a main, non disposable medical unit that can sense the introduction and time of use of the disposable medical accessory product, an ID reader built into the main, non disposable medical unit that does not allow the main medical unit to be turned on if it senses that the disposable medical accessory has already been used before, the ID reader only allowing the main medical unit to be turned on when it senses that the the ID tag on the disposable medical accessory has never been read before, the ID reader to be programmed to accept only particular numbers, known only to the manufacturer, thereby protecting against competitors who do not know the numbers, and An alternate embodiment that also can time the length of cleaning of a medical accessory that is meant to be re used but needs to first be cleaned or sterilized for a predetermined amount of time.

2 Claims, 2 Drawing Sheets

PROCESS FOR CONTROLLING THE MISUSE OF DISPOSABLE MEDICAL PRODUCTS

BACKGROUND OF THE INVENTION

This invention relates generally to the field of medical testing devices, and more particularly to a process for controlling the miss use of disposable medical products.

The use of medical products that have a disposable component to them is ever increasing. For example a new type of dental technology has been developed by the Preio-View Corporation of Cincinnati, Ohio that uses a small camera and fiberscope to view under a patients gum thereby avoiding the need to cut the flap of the gum to view the area. A disposable hygienic sheath is used to cover the permanent fiberscope device so that there is no chance of transferring disease or germ's from one patient to another. The sheaths, although disposable, are rather expensive to purchase, approximately twenty dollars each.

Because of the relative expense of the one time use disposable sheathes there can be a tendency by a dental practitioner to clean and re use the disposable sheath. This protocol is not recommended or desired by the manufacturer because there is a chance of improper or incomplete cleaning, not to mention the loss in revenue from the sale of additional disposable sheaths.

This is only one example of many proliferating medical technology applications that depend on the responsible single use of a disposable medical accessory that interfaces with a piece of permanent medical equipment. At the present time there is no adequate safeguard to help prevent the repeated miss use of supposedly one time use disposable medical products.

SUMMARY OF THE INVENTION

The primary object of the invention is to provide a means for controlling the miss use or repeated use of supposedly one time use disposable medical products.

Other objects and advantages of the present invention will become apparent from the following descriptions, taken in connection with the accompanying drawings, wherein, by way of illustration and example, an embodiment of the present invention is disclosed.

A process for controlling the miss use of disposable medical products comprising the steps of: a unique ID code secured to a disposable medical accessory product, a control circuit built into a main, non disposable medical unit that can sense the introduction and time of use of said disposable medical accessory product, an ID reader built into said main, non disposable medical unit that does not allow said main medical unit to be turned on if it senses that said disposable medical accessory has already been used before, Said ID reader only allowing said main medical unit to be turned on when it senses that the said ID tag on said disposable medical accessory has never been read before, Said ID reader to be programmed to accept only particular numbers, known only to the manufacturer, thereby protecting against competitors who do not know the numbers, and An alternate embodiment that also can time the length of cleaning of a medical accessory that is meant to be re used but needs to first be cleaned or sterilized for a predetermined amount of time.

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
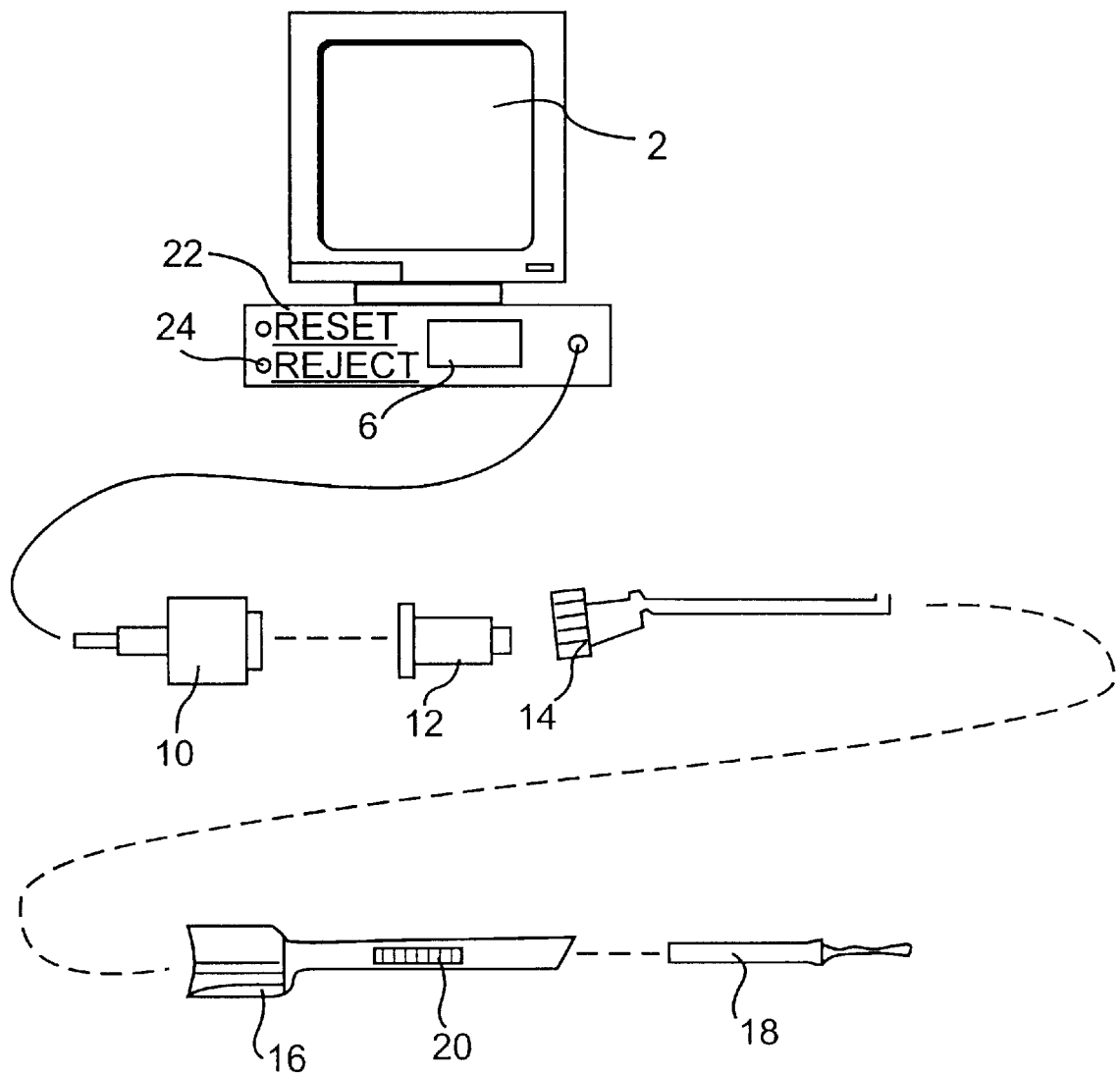
FIG. 1 is a schematic view showing an example of the disposable medical application of the present invention.

Referring now to FIG. 1 we see an application of the disposable medical checking device of the present invention. The application shown involves the PerioView System, a new way of observing gum tissue under the gum line without surgically removing the gum. The calls for the use of a fiberscope 14 attached to a CCD 10 camera. The fiberscope 14 is covered with a protective, disposable sheath 16 that is meant to be replaced for each new patient. Because each disposable sheath costs approximately twenty dollars, there is a temptation of the part of the medical practitioner to clean and re use the disposable sheath. However, the manufacturer of the product has determined that this option is not feasible and that a one time use is mandatory. To this end the camera control box 4 shown in this application includes a version of the present invention in that a bar code reader 6 is built into the front of the camera control box 4. The medical practitioner must pass the disposable sheath 16 over the bar code reader where a bar code 20 printed on the sheath is scanned. A microprocessor built in the camera control box checks the code to see if it has ever been entered before. If not, the "accept" light 22 goes on. If the disposable sheath has been used before, the "reject" light goes on 24 and the signal from the camera 10 is not allowed to be processed by the camera control unit 4. Of course, the manufacturer can program the microprocessor to let the disposable medical accessory be used a number of times if applicable, before disabling the camera. The above described controlling process also insures that other manufacturers can not make and sell unauthorized copies of a disposable medical device because such devices will not have an authorized bar code affixed to the disposable device.

Figure 2:
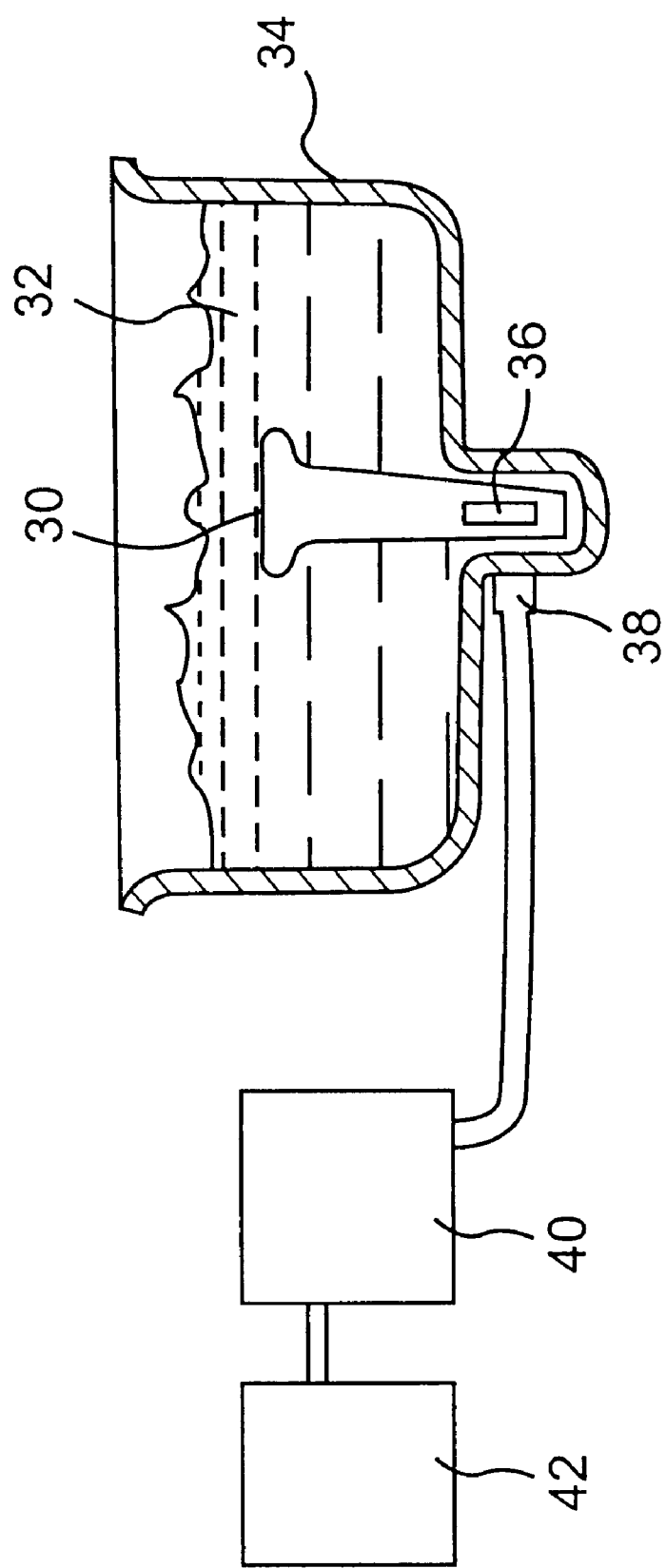
FIG. 2 is a view of a reusable application.

This same concept can be used to apply to applications where a medical item must be cleaned for a certain period of time as shown in FIG. 2. A medical item 30 is placed in a cleaning receptacle 34 that is filled with a cleaning solution 32. An RF tag 36 embedded in the medical item 30 is read by an RF reader 38, identifies that the device is authorized and starts a timing cycle in controller 40 that insures that the item 30 is cleaned for the proper amount of time. Once cleaned controller 40 instructs main medical machine 42 that the medical item 30 is acceptable fro use. The medical item includes an RF tag and is inserted into a mating receptacle in a cleaning solution or the like. The mating receptacle has a built in RF sensor that identifies the medical device as being acceptable and that the item is being cleaned for the proper length of time.

In the above described and illustrated way, a manufacturer of medical equipment can control the uses of disposable medical items that are meant to be used for a particular number of times or to be cleaned for a particular length of time.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A process for controlling the miss use of disposable medical products comprising the steps of:

a unique ID code secured to a disposable medical accessory product;

a control circuit built into a main, non disposable medical unit that can sense the introduction and time of use of said disposable medical accessory product;

an ID reader built into said main, non disposable medical unit that does not allow said main medical unit to be turned on if it senses that said disposable medical accessory has already been used before;

Said ID reader only allowing said main medical unit to be turned on when it senses that the said ID tag on said disposable medical accessory has never been read before;

Said ID reader to be programmed to accept only particular numbers, known only to the manufacturer, thereby protecting against competitors who do not know the numbers.

2. A process for controlling the miss use of disposable medical products as claimed in claim 1 wherein an alternate embodiment can time the length of cleaning of a medical accessory that is meant to be re used but needs to first be cleaned or sterilized for a predetermined amount of time.

* * * * *